United States Patent [19]

Rashbaum et al.

[11] 4,418,081

[45] Nov. 29, 1983

[54] NATURAL RED COLORING PREPARED FROM AN OAT SUBSTRATE

[75] Inventors: Stephan A. Rashbaum, Evanston; Mao Yueh, Barrington, both of Ill.

[73] Assignee: The Quaker Oats Company, Chicago, Ill.

[21] Appl. No.: 280,617

[22] Filed: Jul. 6, 1981

[51] Int. Cl.³ .................. A23L 1/27; A23L 1/28; C12P 1/02; C12N 1/14

[52] U.S. Cl. .................................. 426/18; 426/250; 426/270; 435/171; 435/254; 435/911

[58] Field of Search ............ 426/250, 270, 44, 18; 435/911, 171, 254

[56] References Cited

U.S. PATENT DOCUMENTS

| | | | |
|---|---|---|---|
| 3,243,301 | 3/1966 | Hesseltine et al. | 426/18 |
| 3,615,674 | 10/1971 | Bass et al. | 426/250 |
| 3,765,906 | 10/1973 | Yamaguchi et al. | 99/148 |
| 3,885,048 | 5/1975 | Liggett | 426/18 |
| 3,911,141 | 10/1975 | Farr et al. | 426/60 |
| 4,031,250 | 6/1977 | Haas et al. | 426/18 |
| 4,145,254 | 3/1979 | Shepherd et al. | 426/250 |

FOREIGN PATENT DOCUMENTS 498123 12/1953 Canada ................ 426/250

*Primary Examiner*—Raymond N. Jones
*Assistant Examiner*—Elizabeth J. Curtin
*Attorney, Agent, or Firm*—Karen E. Ayd; G. T. Shekleton; J. P. O'Halloran

[57] ABSTRACT

A food product is prepared having a red-meaty color imparted thereto by the incorporation of an effective amount of pigments produced by the growth of the mold of the genus Monascus on an oat substrate.

4 Claims, No Drawings

NATURAL RED COLORING PREPARED FROM AN OAT SUBSTRATE

BACKGROUND OF THE INVENTION

This invention relates to food products and more particularly to the coloring of such food products to obtain a meaty-red color.

Food colorant agents for meats, whether they be for human or pet foods, are generally formulated to give the appearance of real meat in both color and texture. Use of the pigments produced by the growth of the mold *Monascus purpureus* on material selected from rice and corn has been taught for use as food coloring when added to food products by U.S. Pat. Nos. 3,911,141, 4,031,250, and 4,145,254 and others. Such treated rice or corn is generally subdivided and used per se as the coloring material. The corn or rice thereby serves both as a nutrient source as well as a colorant in the food.

To date there have been no teaching that molds of the genus Monascus, such as *Monascus purpureus* could be successfully cultivated on an oat substrate and thereby take advantage of oats' excellent nutritive and other helpful qualities. The oat groat is unique in structure, composition, processing, organoleptic properties, and nutritive values; because of such uniqueness, experiences with other grains may not be easily transferred to oat. For instance, the gum content of oat is greatly in excess of that of other grains. Oat starch is regarded as markedly different from wheat and corn starch, probably due to the more branched structure of oat starch, as well as its occurrence as compound granules. In addition the lipid content of oats is the highest of all grains, as well having the highest level of lipase and protein of any of the cereal grains. Other differences, such as those engendered by the different milling procedure for oats, are in abundance. These differences, when viewed in the aggregate, result in a grain by which the uses and generalizations applicable to the other grains may not be applied. For instance, other grains such as wheat and rice and corn generally have no difficulty in storage of the whole grain. However, whole grain oats are stored only with great difficulty having problems with rancidity and the like. In addition, it is known that whole oat groats will not support the uniform and efficient growth of molds of the genus Monascus in any known medium in the same manner as will other grains, such as rice and corn. Because of this different status accorded oats, there have been no successful attempts to cultivate molds of the genus Monascus on oats, even though rice or corn have been used successfully as substrates.

SUMMARY OF THE INVENTION

It is therefore an object of the subject invention to produce a red color through the fermentation of molds of the genus Monascus on a substrate of oats.

It is another object of the subject invention to provide a red-meaty color in food products through the incorporation of pigments produced by the growth of molds of the genus Monascus on a solid or liquid substrate of oats.

A further object of the subject invention is an improved process for the production of a red color on a substrate such as oats in a fast and efficient manner.

These and other objects are attained in accordance with the present invention wherein there is provided pigments produced by the growth of molds of the genus Monascus on materials selected from either steel cut and tempered oats or oat flour; such treated material can be used directly as a food coloring agent for supplying a meaty-red color to the food product. The pigments produced through the method of the subject invention stain the oat substrate which may be dried, ground, and utilized as an integral part of the food product being colored. For instance, in pet foods the stained oats may be used as a direct replacement for the grain content of the pet food. As stated, the substrate used in the culturing of molds of the genus Monascus may be either a solid substrate utilizing steel cut oat grains or a liquid substrate utilizing an aqueous nutrient medium and oat flour under aerobic conditions. In addition a greatly reduced fermentation time is gained over the methods of the prior art, while still yielding color of the intensity desired.

DETAILED DESCRIPTION OF THE INVENTION

Further objects of the invention together with additional features contributing thereto and advantages accruing therefrom will be apparent from the following description of several embodiments of the invention.

The strain of a microorganism of the genus Monascus which produces pigment of the monascorubrin or rubropunctatin type may be used for carrying out the process according to the subject invention. An inoculum of the strain selected may be prepared from a reconstituted, freeze dried culture, or from a culture on a solid or liquid medium by any method known in the art.

In general the method of the subject invention involves preparing the substances to be inoculated in a moist or aqueous fashion. This substance or substrate is sterilized by moist heat to temperatures above 100° C. In a preferred embodiment of the subject invention, a simple autoclave process with temperatures typically in excess of 100° C., and generally 121° C. at 15 psi pressure for about 15 minutes, or, a period of time sufficient to kill any viable microorganism and to gelatinize any starch contained within the substrate so as to make it available to molds of the genus Monascus, is used. The substrate contained in the sterile vessel is then inoculated with the Monascus mold so that the viable organism is evenly distributed throughout the growth substrate and then allowed to ferment unhindered until completion of its growth cycle, as monitored by the completion of coloration of the substrate. The moisture level is maintained at approximately 30% throughout the cycle of the organism by addition of water as necessary. The colored substrate may then be dried, ground, and utilized as a food colorant.

When a liquid substrate is preferred, an aqueous, nutritious solution must first be prepared such as through the mixture of magnesium sulfate, sodium nitrate, and potassium phosphate and blending this nutrient solution with oat flour. For the deepest, most vivid color, the concentration of the nutrient solution should be such as to permit optimum growth of the mold of the substrate as known in the art. From a practical viewpoint, the salt concentration must be higher if more oats are included as substrate. The nutrient solution may include amino acids, sugars, starches, protein hydrolysates, molasses, casein, yeast and other ingredients as known in the art. The oat solution is then sterilized, such as through autoclaving as stated above, and cooled. The resulting sterilized oat solution is placed in a glass flask, inoculated, and aerated by continuous shaking at intermediate speeds until the growth cycle of the Monascus mold is complete. Such shaking speeds up the growth of the mold as well as pigmentation of the substrate. The resulting colored substrate may be collected by centrifugation, drying, and grinding to a desired particle size. Colored substrate may then be used through addition to food products as desired.

Concentration of the nutrient solution may be varied as desired. In fact, the oats will support growth of the *Monascus purpureus* mold in simply an aqueous solution, although the color strength may be less deep and vivid than if a nutrient solution was used.

The invention is better illustrated through reference to the following examples:

EXAMPLE I

Grade A oat groats were cut so that each individual piece of grain would be fractured into no more than three pieces. 50 grams of this oat substrate was immersed in excess water for 5 minutes after which time the excess water was removed by draining through cheesecloth and squeezing in cheesecloth bag. The moistened groats were placed in a 500 ml flask and sterilized by autoclaving at 121° C. for 15 minutes. The sterile vessel was inoculated with previously grown culture of *Monascus purpureus* and incubated at 25° C. until the maximum amount of coloration had appeared—approximately 3 weeks. Again, water was added as necessary to maintain the moisture content of the grain, around 30%. After the incubation period, the grain was harvested and examined. The grain was found to be a rich red on the surface and with the same color extending down past the surface of the particle grain extending through the entire interior of each piece of grain. The color was evenly distributed throughout the entire culture and most suitable for future use, such as by inclusion in a pet food as a direct substitute for the grain content of the pet food.

EXAMPLE II

Food colorants were prepared through the fermentation of *Monascus purpureus* with oat flour in a submerged nutrient culture. The nutrient culture comprises a suitable salt-supplemented solution, the salts being chosen to provide both buffering capacity and essential mineral nutrients for the growth of the organism. 10 grams of No. 36 oat flour were added to a 500 ml flask containing 100 ml water, 0.2% $MgSO_4.7H_2O$, 0.3 $NaNO_3$ and 0.5% $KH_2PO_4$. After sterilization and inoculation, either from a water washed slant or previously grown liquid culture, the flask was placed on a platform shaker and incubated at 25° to 30° C. with agitation sufficient to supply adequate aeration, typically 225 rpm, for approximately 48 hours, at which time the coloration of the substrate was complete. The colored substrate was collected by centrifugation, and dried prior to use, typically by freeze drying or air drying.

EXAMPLE III

In a manner similar to that in Example 2, grade A groats steel cut as in Example 1 were added to a solution containing 0.2% $MgSO_4.7H_2O$, 0.3% $NaNO_3$, and 0.5% $KH_2PO_4$, typically 10 grams into 100 ml solutions in a 500 ml flask. After sterilization and inoculation, as above, the solution was shaken to provide aeration, typically 225 rpm at 25° C. The colored substrate was produced under these conditions typically in 48-72 hours. The material was harvested and dried as in Example 2.

EXAMPLE IV

The dried colored substrate prepared as in Examples 1, 2 and 3 was each milled to a consistency similar to that of flour. This powdered material was found to be effective in imparting a meatlike color to both humans and pet foods. Concentration varied from 0.05% to 5.0% depending upon the formulation of the pet food and the color intensity desired.

In each of the examples set forth above it was noted that, in a dog food product, commonly termed burger, which has been colored with the *Monascus purpureus* cultured oats, little or no permanent discoloration of either nylon or wool carpeting was observed when treated with a mixture of burger and simulated gastric juices (0.5% HCl, 5 mg/ml pepsin and 1 mg/ml lipase). In other words the initial color stain was easily removed with a standard cleaning solution. Commercially available burger, colored with FD+C Red #40 or Aluminum Red #40 Lake, when mixed with the simulated gastric juice and applied to the carpeting left a permanent stain that was not removable by standard techniques.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

We claim:

1. A method for imparting a red, meaty color to a food product comprising culturing a mold of the genus Monascus which produces pigment of the Monascorubrin or Rubropunctatin type on an oat substrate to obtain red pigments thereon, drying and subdividing said oat substrate into a finely-divided form, and adding said finely divided substrate to said food product in an amount effective to impart a red color to said food product, wherein the step of culturing the Monascus mold comprises:
   a. cutting oat groats so that each oat groat is cut into at least three individual pieces;
   b. moistening said cut oat groats to about 30% moisture content and sterilizing said moistened groats;
   c. innoculating and culturing said sterilized moist, cut oat groats with a Monascus mold selected from the group of Monascus mold which produces pigments of the Monascorubrin or Rubropunctatin type;
   d. maintaining said moisture level at about 30% throughout said culturing step; and
   e. incubating said Monascus mold on said oat substrate.

2. A method for imparting a red, meaty color to a food product comprising culturing a mold of the genus Monascus which produces pigment of the Monascorubrin or Rubropunctatin type on an oat substract to obtain red pigments thereon, drying and subdividing said oat substrate into a finely-divided form, and adding said finely divided substrate to said food product in an amount effective to impart a red color to said food product, wherein the step of culturing the Monascus mold comprises:
   a. preparing a nutrient solution;
   b. adding one part of an oat substrate selected from the group of oat flour and cut oat groats to 10 parts of nutrient solution to form an oat suspension;
   c. inoculating said oat suspension with the Monascus mold;
   d. agitating said inoculated oat suspension to aerate the suspension; and
   e. incubating the Monascus mold in said aerated suspension to yield a red-pigmented oat substrate.

3. The method of claim 2 wherein the nutrient solution is prepared by mixing less than 1% by weight of $MgSO_4$, $KH_2PO_4$ and $NaNO_3$ with water.

4. The method of claim 2 wherein the nutrient solution includes at least one ingredient selected from the group amino acids, sugars, starches, protein hydrolysates, molasses, casein, and yeast.

* * * * *